United States Patent
Heyne et al.

(10) Patent No.: US 9,560,989 B2
(45) Date of Patent: Feb. 7, 2017

(54) METHOD FOR DETERMINING THE METABOLIC CAPACITY OF AT LEAST ONE ENZYME

(75) Inventors: Karsten Heyne, Grossbeeren (DE); Martin Stockmann, Berlin (DE); Tom Rubin, Berlin (DE)

(73) Assignee: HUMEDICS GMBH, Berlin (DE)

( * ) Notice: Subject to any disclaimer, the term of this patent is extended or adjusted under 35 U.S.C. 154(b) by 527 days.

(21) Appl. No.: 14/111,165

(22) PCT Filed: Apr. 13, 2012

(86) PCT No.: PCT/EP2012/056808
§ 371 (c)(1),
(2), (4) Date: Dec. 6, 2013

(87) PCT Pub. No.: WO2012/140213
PCT Pub. Date: Oct. 18, 2012

(65) Prior Publication Data
US 2014/0107516 A1    Apr. 17, 2014

(30) Foreign Application Priority Data

Apr. 13, 2011  (DE) .......................... 10 2011 007 310

(51) Int. Cl.
*A61B 5/08*    (2006.01)
*A61B 5/083*    (2006.01)
(Continued)

(52) U.S. Cl.
CPC .............. *A61B 5/0836* (2013.01); *A61B 5/087* (2013.01); *A61B 5/0813* (2013.01); *A61B 5/097* (2013.01);
(Continued)

(58) Field of Classification Search
USPC ........................................................ 600/531
See application file for complete search history.

(56) References Cited

U.S. PATENT DOCUMENTS

| 5,964,712 A | 10/1999 | Kubo et al. |
| 2003/0171687 A1 | 9/2003 | Irie et al. |
| (Continued) |

FOREIGN PATENT DOCUMENTS

| CN | 1177399 A | 3/1998 |
| JP | 2008-538275 A | 10/2008 |
| (Continued) |

OTHER PUBLICATIONS

Strickland SI, Palmer GR, Massey VI. Determination of dissociation constants and specific rate constants of enzyme-substrate (or protein-ligand) interactions from rapid reaction kinetic data. Journal of Biological Chemistry. Jun. 10, 1975;250(11):4048-52.*

(Continued)

*Primary Examiner* — Michael Kahelin
*Assistant Examiner* — Mitchell E Alter
(74) *Attorney, Agent, or Firm* — Maschoff Brennan

(57) ABSTRACT

A method for determining the metabolic capacity of an enzyme includes time-resolved determination of the concentration of a product in exhaled air. The product is created by metabolism of a substrate, previously administered to an individual, by an enzyme of the individual. The product concentration is determined until the maximum product concentration in the exhaled air is reached. A model function is fitted to measured values of the product concentration, obtained by the time-resolved determination of the product concentration between start and end times. The metabolic capacity of the enzyme is determined based on parameters of the model function. Determining the metabolic capacity of the enzyme takes place based on at least two parameters of the model function, wherein the maximum value and time constant of the model function are not selected as parameters at the same time, and the start and/or end times are not selected as parameters.

23 Claims, 1 Drawing Sheet

(51) Int. Cl.

| | |
|---|---|
| *A61B 5/097* | (2006.01) |
| *A61B 5/087* | (2006.01) |
| *A61B 5/00* | (2006.01) |
| *G01J 3/42* | (2006.01) |
| *G01R 33/465* | (2006.01) |
| *G01T 1/29* | (2006.01) |
| *H01J 49/26* | (2006.01) |

(52) U.S. Cl.
CPC .. *A61B 5/72* (2013.01); *G01J 3/42* (2013.01); *G01R 33/465* (2013.01); *G01T 1/2985* (2013.01); *H01J 49/26* (2013.01)

(56) References Cited

U.S. PATENT DOCUMENTS

| | | |
|---|---|---|
| 2005/0061321 A1 | 3/2005 | Jones |
| 2007/0026480 A1 | 2/2007 | Modak et al. |
| 2008/0279766 A1 | 11/2008 | Everson et al. |
| 2009/0298070 A1 | 12/2009 | Lee et al. |

FOREIGN PATENT DOCUMENTS

| | | |
|---|---|---|
| JP | 2009-516534 A | 4/2009 |
| JP | 2009-534028 A | 9/2009 |
| WO | 2007/000145 A2 | 1/2007 |
| WO | 2010/013235 A2 | 2/2010 |

OTHER PUBLICATIONS

Zeng Wenbing et al: "13C-methacetin breath test parameter S for liver diseases diagnosis", Feb. 1, 1996, pp. 87-89, XP007920729.

G. Lalazar et al: „A continuous 13C methacetin breath test for noninvasive assessment of intrahepatic inflammation and fibrosis in patients with chronic HCV infection and normal ALT, Feb. 2008, 716-728.

Chinese Office Action for corresponding application No. CN 2014-504344, mailed May 10, 2016.

* cited by examiner

METHOD FOR DETERMINING THE METABOLIC CAPACITY OF AT LEAST ONE ENZYME

CROSS-REFERENCE TO A RELATED APPLICATION

This application is a national phase patent application of International patent application PCT/EP 2012/056808, filed on Apr. 13, 2012, which claims priority of German patent application 10 2011 007 310.8, filed on Apr. 13, 2011, and of U.S. provisional patent application 61/476,113 filed on Apr. 15, 2011.

BACKGROUND

The invention relates in an aspect to a method for determining the metabolic capacity of at least one enzyme and the use of various $^{13}C$-labeled substrates in such a method, respectively.

Enzymes significantly contribute to the degradation of harmful substances in the body of animals and humans. There is a multitude of various enzymes, e.g. cytochromes, which catalytically convert substrates.

As the enzymes or enzyme systems (in what follows reference will always only be made to enzymes while both will be meant) exert important functions, it is of high importance to determine their functional capacity in an organism. This happens nowadays e.g. via examinations directly on the cell cultures outside of the organism, which has the disadvantage that the enzyme is not examined in its native environment. Examinations in the organism typically involve the administration of isotope-labeled substrates, which are metabolized by the enzyme. The administration or application takes place either by surgical interventions, such as e.g. the direct injection into the heart, or else by other methods, such as e.g. taking the substrate orally.

The non-surgical applications here almost always have the disadvantage that the availability of the substrate in the blood takes several minutes. That is to say, the time period at the start of which the concentration of the substrate S in the blood increases until it has taken on a maximum concentration (without taking into account possible decreases in concentration by metabolism) takes several minutes.

An alternative is the high-sensitive detection of trace gases without prior administration of a substrate. But that has the disadvantage that the exact anamnesis of the examined individual and all the causes for the enrichment of a gas in the breathing air must be known. As a matter of principle, however, this anamnesis cannot be determined accurately enough.

SUMMARY

The object underlying an aspect of the present invention is to provide a method, by which the metabolic capacity of an enzyme can be determined highly precise and time-resolved. Moreover, suitable substrates for such a method shall be provided.

This object is achieved with a method having the features of Claim 1. Such a method for determining the metabolic capacity of at least one enzyme comprises the subsequently explained steps.

First, a time-resolved determination of the concentration of a product in the air exhaled by an individual takes place. The product is here generated by a metabolism of a substrate, previously administered to the individual, by at least one enzyme of the individual. Often entire enzyme systems are participating in the metabolism of a corresponding substrate. The product concentration is determined at the least until the maximum product concentration in the air exhaled by the individual is reached.

Subsequently, a model function is fitted to measured values of the product concentration, which were obtained by the time-resolved determination of the product concentration between a start time and an end time. That is to say, the empirically obtained measured values are fitted by a mathematic function, which can be specified by an equation.

Finally, the metabolic capacity of the enzyme is determined on the basis of parameters of the model function which specify the model function. For this purpose, various parameters of the model function can basically be used.

What is special about the method claimed is that determining the metabolic capacity of the enzyme takes place on the basis of at least two parameters of the model function. These parameters may not, however, be the maximum value of the model function and the time constant of the model function at the same time, particularly not when the model function is a mono-exponential function. Moreover, the start time $t_0$ and/or the end time $t_m$ of the model function may not be selected as parameters.

When these basic conditions are fulfilled, differently progressing metabolism kinetics of a variety of substrates and thus a diversity of product generation kinetics can be analyzed, to ultimately be able to determine the metabolic capacity of an enzyme or an enzyme system. The selected parameters of the model function allow for direct conclusions about the metabolic capacity of the enzyme. The metabolic capacity of an enzyme can serve as a basis for the quantitative determination of the state of health of an individual concerning specific bodily functions. This can take place in subsequent steps of the process. As enzymes occur in a diversity of organs or compartments of the body, the present method is suited as a basis for numerous subsequent examinations. In an embodiment, the method can form the basis to analyze the condition of the liver which is characterized for instance by the liver function capacity or the microcirculation in the liver.

In order to obtain reliable and significant data of the determined metabolic capacity of the enzyme, ensuring a rapid availability of the substrate in the blood of the individual is well suited. An oral ingestion of the substrate is generally unsuitable for this purpose.

The temporal dependency of the substrate concentration in the blood (without metabolism) is specified by the function S(t). In order to give a more accurate definition of the availability or release of the substrate in the blood, let the release period FZ be defined here. Let $C_{max}$ be the expected maximum substrate concentration in the blood (without metabolism), $t_0$ the moment in time, in which the substrate concentration in the blood has increased to 4% to 6% of $C_{max}$, and $t_m$ the moment in time, in which the substrate concentration in the blood has increased to 40% to 60% of $C_{max}$, particularly, in which the substrate concentration in the blood lies above 40%, above 50% or above 60% of $C_{max}$, then the release period FZ is given by the time difference between $t_m$ and $t_0$ ($FZ=t_m-t_0$). In other words, the release period is the time period that is needed to reach an increase of the substrate concentration in the blood (proceeding on the assumption that the concentration lies slightly above 0% of $C_{max}$, however, still in a single-digit percent range of $C_{max}$) by a factor of 10, particularly by a factor of 12, particularly by a factor of 15 and especially by a factor of 20.

The release period for a standard oral administration of a substrate is typically more than 5 minutes and varies considerably inter-individually from day to day. For this reason, administrations with a long release period lead to distorted results, because the measuring results are convoluted with the function S(t) and consequently "blurred" with a function which is unknown.

The long release periods, known from prior art, and the accompanying disadvantages when subsequently the metabolic capacity of an enzyme is determined can be avoided by a targeted induction of the metabolism apparatus of the individual, that is to be examined, by means of a non-surgical administration of a substrate. For the targeted induction the dosage of the substrate is predetermined, so that in the subsequent steps of interpretation the reaction of the metabolism apparatus concerning the dosage of the substrate can be estimated. In an embodiment, solely gases are examined as products, the concentration of which changes by induction of the metabolism apparatus as a result of the administration of the substrate. The induction of the metabolism apparatus by the substrate and the answer of the metabolism following rapidly thereupon is a key point for the subsequent application of the method claimed.

In an embodiment the explained targeted induction of the metabolic apparatus is a part of the method which is preceding the step of the time-resolved determination of the concentration of the product.

The administration and the release of the substrate, which is depending on the kind and manner of administration, best takes place in such a way that the release period (and thus the availability of the substrate in the blood) is faster than 60 seconds, particularly faster than 50 seconds, particularly faster than 40 seconds, particularly faster than 30 seconds, particularly faster than 20 seconds and especially faster than 10 seconds.

The substrate is hence best administered in a dosage form which allows for a release time of the substrate in the blood of the individual within the aforementioned times. Such a short release period can basically be achieved by various forms of administration or applications. Without limiting interpretation a few shall be presented here: a) inhalation of an aerosol which contains the substrate, b) administration via the skin, e.g. with efficient nanocarriers, c) orally taking a switchable (in particular activatable) substrate, which is released by energy absorption. After being orally administered, the substrate, which in the bound state is non-degradable, can thus be completely released within a second by application of energy, particularly by light. Such substrates in the bound state are also called caged compounds in technical terms. The use of such caged compounds allows for an ultra-rapid and selective release of the corresponding metabolizable substrate, inducible anytime.

The rapid availability of the substrate in the blood guarantees the rapid availability of the substrate on the enzyme, the metabolic capacity of which is to be examined.

When the substrate exists in the blood and lies on the enzyme, it can be metabolized by the enzyme. Thereby, the product is or the products are generated, which will ever only be referred to as an individual product below. The steps of metabolism have to be very rapid and best be completed within 10 seconds, particularly within 5 seconds, particularly within 1 second, particularly within 0.1 seconds, particularly within 0.01 seconds, particularly within 0.001 seconds. On the time scale of the availability of the substrate this guarantees a virtually instantaneous metabolism. The product or the products P, formed during the metabolism of the substrate, is/are dissolved in the blood and exhaled via the lung, so that it/they can then be detected in the air exhaled by the individual. Even if reference is presently ever made to only one product, embodiments of the method are also comprised thereby in which not only an individual product but multiple products are detected.

To specify the metabolic capacity of the enzyme different parameters of various fitting functions can be used. Examples of suitable parameters are parameters from the group comprising the maximum value of the model function, the i-th moment of the model function with i=1, 2, 3, 4, . . . , the j-th central moment of the model function with j=1, 2, 3, 4, . . . , the standard deviation of the model function, a time constant of the model function, the centre of gravity of the time constants, the mean deviation of the time constants from the centre of gravity, the variation of the time constants, the distribution of the time constants, the weighting of the time constants, the weighting of the distribution of the time constants, the weighting of the variation of the time constants.

The moments of a model function are for instance explained in the Handbook of mathematics by Bronstein and Semendjajew (p. 665 to 668, $25^{th}$ ed., 1991). In this reference also numerous other model functions and model parameters can be found, which can be used individually or in combination with each other within the scope of the present teaching.

An example of two parameters which are well suited to specify the model function are the maximum concentration or amount $P_{max}$ of the product P in the breathing air and the first moment of the model function from $t_0$ to $t_m$. The first moment $M_1$ is defined by:

$$M_i = \sum_k t_k^i p_k,$$

$M_i = \Sigma_k t_k^i p_k$ with i=1, wherein the sum is calculated over all measuring points k between $t_0$ and $t_m$. Here, $t_k$ is the time of the k-th measuring point and $p_k$ the measured value of the concentration of the product P in the breathing air at the time $t_k$.

A further example of two parameters which are well suited to specify the model function are the maximum concentration or amount $P_{max}$ of the product P in the breathing air and the second central moment of the model function from $t_0$ to $t_m$. The second central moment $MZ_2$ is defined by:

$$MZ_i = \sum_k (t_k - M_1)^i MZ_i = \sum_k (t_k - M_1)^i,$$

with i=2. The second central moment is the variance of the first moment and gives the width of the distribution of the rising function of the examined metabolism.

Further combinations of parameters, e.g. of $P_{max}$, $M_1$ and $MZ_2$, as well as of higher moments, higher central moments or other parameters, particularly the other parameters mentioned above, are possible and give, depending on the examined enzyme, direct information about the metabolic capacity of the enzyme.

The model function can basically have one or multiple time constants. For instance, in the case in which a combination of multiple functions is used as model function, the model function has multiple time constants. The existence of multiple time constants is a prerequisite for the fact that for instance the centre of gravity of the time constants, the mean deviation of the time constants from the centre of gravity, the variation of the time constants, the distribution of the time constants, the weighting of the time constants, the weighting of the distribution of the time constants or the weighting of the variation of the time constants can be selected as parameters.

In an embodiment, the model function (or fitting function) is a solution function of a first order differential equation, a solution function of a second order differential equation, a solution function of a third order differential equation, a solution function of a combination of differential equations of various orders or a multi-exponential function as a function of time. When a combination of differential equations of various orders is used, the solution function can also include contributions of a zero order differential equation.

To allow for an especially simple measurement of the exhaled air and to achieve a high accuracy of the measurements at the same time, whereby the informative value of the obtained measured values improves significantly, determining the concentration of the product best takes place in flow-through.

By an absorption measurement according to the Beer-Lambert law with a known extinction coefficient and a known path length of the measuring cell the concentration of the examined substance can immediately be obtained. In an embodiment, furthermore also the flow rate of the exhaled air, which flows through a measuring apparatus used to determine the concentration, is determined. Then, the amount of the examined product can be calculated from the product of the concentration and the volume, which flowed through the measuring apparatus. The volume, which flowed through the measuring apparatus, is obtained by a multiplication of the volume flow with the time within which the volume flow is observed.

The breathing resistance of the measuring instrument is, in an embodiment, less than 100 mbar, particularly less than 80 mbar, particularly less than 70 mbar and especially less than 60 mbar. This is achieved for instance by an open structure without valves and without air flaps.

The increase of the product in the blood is mirrored proportionally in the breathing air. The amount or concentration of the product is measured in the breathing air as a function of time. In one embodiment the exhaled air is to the full extent (completely) channelled through a measuring instrument, by means of which the product is detected. That is to say, in this embodiment the entire exhaled air of at least one breath of the individual is used as exhaled air. Thus, the concentration of the product in the breathing air can be determined in an especially suited manner while minimizing the measurement error by not using interpolations.

In another embodiment the exhaled air of a breath or of multiple breaths (about 2 to 20 breaths, particularly 3 to 15 breaths, particularly 4 to 10 breaths, particularly 5 to 8 breaths) is completely mixed together, and a part of this mix is then channelled through a measuring instrument, by means of which the product is detected.

In order to obtain data which can be reproduced especially well the examined individual should best be positioned in a stable phase while determining the product concentration in the breath. With humans and animals this can for instance be ensured by not subjecting the organism to strong movements during the determination of the product concentration in the exhaled air. For instance, e.g. in the lying state of the individual, lifting the legs by 45 degrees from the horizontal position can change the measured values of the concentration of the product in the breathing air. On account of the storage function of the blood and its distribution in the organism, walking, running or standing-up movements lead to changed values of the concentration of the product in the exhaled air. Hence, determining the concentration of the product best takes place while the individual is essentially in a resting position. This resting position can be a lying or sitting position. It is suited when the position of the legs and/or of the upper part of the body of the individual is changed by less than 45 degrees, particularly by less than 30 degrees and especially by less than 15 degrees compared with the predetermined position. In the lying position of the individual this predetermined position is for instance an essentially horizontal position of the individual.

In an embodiment, only the rise in the concentration of the product (namely the metabolism dynamics) is analyzed up to the maximum. This maximum corresponds to the maximum concentration of a product in the air exhaled by the individual. In an embodiment, this rise takes less than 40 minutes, particularly less than 20 minutes and especially less than 10 minutes. The longer the rise takes, the more likely it becomes that the body's own processes can influence the result, whereby the overall accuracy of the obtained measuring data decreases.

The execution of the method presently claimed with the help of NMR spectroscopy and/or CT takes place slightly divergent to an execution by means of infrared spectroscopy and/or mass spectrometry. NMR spectroscopy and CT are imaging measurement methods and can be employed for instance in the following manners:

a) By means of NMR spectroscopy and CT the spatial area of interest is examined. Additionally, the product in the breathing air is analyzed. A comparison of both measurements provides new information.

b) By means of NMR spectroscopy and CT the spatial area of interest is examined, while additionally the product in the exhaled air is analyzed. A comparison of the chronological sequences of both measurements provides new information. NMR spectroscopy and CT can herein trace the increase and decrease of the product concentration in a spatially resolved manner. The use of isotope-labeled substrates or of substrates with high electron density here allows for the use of NMR-spectroscopy and CT in an especially suited manner.

In order to allow for a comparison with other individuals, a normalization with respect to the bodyweight of the examined individual is done in an embodiment. In particular, such normalization can be carried out by dividing the obtained value being indicative for the metabolic capacity by the body weight of the individual. In case that the body weight is already considered in the model function being used for obtaining an according value being indicative for the metabolic capacity, the body weight is considered twice during the whole method. As an example, it is conceivable that the value being indicative for the metabolic capacity bears a unit in which $kg^2$ is present in the denominator. This would be the result from two consecutive divisions by the body weight of the individual (or one division by the square of the body weight of the individual).

In an embodiment, the model function can be expressed by the following formula:

$$\text{MetPow} = cal * [F(product,t) - f(product,t)_{nat}] * g(P) * h(n) * L(n/M) * (n/M^2) * V(n/M),$$

wherein
  MetPow denotes the metabilic capacity,
  cal is a constant taking into account corrections, F(product,t) is a function expressing the dynamics of exhaled product, f(product,t)$_{nat}$ is a function expressing the natural abundance of the product in the air exhaled by the individual prior to substrate administration, g(P) is a function expressing the dependence of the product production rate P of the individual on the activity status of the individual, h(n) is a function expressing the number of product molecules generated per substrate molecule, L(n/M) is a function expressing a non-linear behaviour of the metabolic capacity dependent on the number of administered substrate molecules n, wherein M denotes the bodyweight of the individual, and V(n/M) is a function expressing dependencies due to different administration procedures of the substrate.

All of these individual functions and constants of the exemplary model function will be explained in more detail in the following with respect to a specific embodiment relating to $^{13}CO_2$ as product of the metabolism of a $^{13}C$-labeled substrate. These explanations are not to be construed as limiting for the general formula of MetPow indicated above, but will help understanding the individual parameters of this model function better.

An example of the claimed method is the determination of the metabolic function of an organ, e.g., the liver, measured via metabolic dynamics of a $^{13}C$-labeled substrate by means of determination the metabolic capacity of an enzyme. A possible substrate is $^{13}C$-methacetin that is metabolized to $^{13}CO_2$ and paracetamol in the liver cells by the enzyme CYP450 1A2. Other substrates, such as $^{13}C$-caffeine, are also suitable for an according determination.

The dynamics of the metabolism generated $^{13}CO_2$ provides information on the metabolic function of the liver or other organ. Unfortunately, $^{13}CO_2$ has a natural abundance of about 1.1% of the total $CO_2$ in the human body. Thus, one has to discriminate between the natural abundance in the body and the additional $^{13}CO_2$ generated by substrate metabolism in the liver. Other substrates with different metabolism products may not suffer from these limitations. A common way to determine the natural abundance of $^{13}CO_2$ in the body is to measure the ratio of $^{13}CO_2$ and $^{12}CO_2$ before administration of the substrate. Depending on the measurement procedure the natural abundance will be calculated by a function f($^{13}CO_2$, $^{12}CO_2$)$_{nat}$. Two possible examples for this function are:

$$f(^{13}CO_2,^{12}CO_2)_{nat}=k1*^{13}CO_2/^{12}CO_2*0.011,$$

with a constant number k1;
or $$f(^{13}CO_2,^{12}CO_2)_{nat}=k2*(k3*^{13}CO_2-^{12}CO_2)/(^{13}CO_2-^{12}CO_2),$$

with constant numbers k2 and k3.

Other functions are also possible. In particular, if the natural abundance of $^{13}CO_2$ in the body is determined over a certain period of time or is expressed as a mean value of different measurements at distinct time points, a dependency of time is to be considered. Then, this function is to be written as f($^{13}CO_2$, $^{12}CO_2$, t)$_{nat}$. If no time dependency exists, f($^{13}CO_2$, $^{12}CO_2$, t)$_{nat}$ is equal to f($^{13}CO_2$, $^{12}CO_2$)$_{nat}$.

In order to determine the metabolic function from the dynamics of the exhaled $^{13}CO_2$ or from the dynamics of the exhaled ratio of $^{13}CO_2/^{12}CO_2$, the function F($^{13}CO_2$, $^{12}CO_2$, t) is used. The easiest form of function F is to take the maximal value of the dynamics at time $t_{max}$. Another option is to use the first or second moment of the dynamics or to use a combination of the area under the curve up to the maximal value, the area under the curve up to the half value of the maximum and the duration of these time points. Other combinations are also possible using functions described above.

In an embodiment, the total function describing the liver metabolic power MetPow (being identical to the metabolic capacity of a selected enzyme) is given by the following formula:

$$MetPow=cal*[F(^{13}CO_2,^{12}CO_2,t)-f(^{13}CO_2,^{12}CO_2,t)_{nat}]*g(P_{CO2})*h(n)*L(n/M)*(n/M^2)*V(n/M)$$

In this formula, the constant number cal takes into account corrections, in particular due to calibration of experiments and due to medical applications.

$P_{CO2}$ denotes the total $CO_2$ production rate which depends on the activity status of the breathing individual (resting or sporting) that determines the natural $^{12}CO_2$ and $^{13}CO_2$ values in the exhaled air. Thus, the total $CO_2$ production rate is here described by the function g($P_{CO2}$). In the simplest case of a resting individual the function is given by g($P_{CO2}$)=k4*$P_{CO2}$, with k4=1.

The function h(n) describes the part of molecules that will be metabolized by the liver into $^{13}CO_2$. The number of substrate molecules n is given in mol. Depending on the substrate it can vary between x and 0, x being a number higher than 0. Highly functional substrates have values of x near to or above 1. A substrate with x=3 means that per substrate molecule 3 molecules of $^{13}CO_2$ will be generated by metabolism.

The function V(n/M) describes dependencies due to various administration procedures of the substrates. For example, oral and intravenous administrations result in different metabolic processes and time constants. These differences are corrected by the function V(n/M).

Since the number of metabolized substrate molecules increases with increasing substrate molecules, the measured signal values of the dynamics increase with increasing number of substrate molecules. For liver metabolism it is useful to administer a specific amount of molecules per square body weight $M^2$. This takes into account that the liver increases its power with increasing square body weight. Thus, the metabolic liver power is proportional to $n/M^2$.

Finally, due to distribution processes within the body, diffusion and transport processes in the cellular membranes of the liver cells, the determined metabolic liver power "MetPow" depends nonlinear on the number of administered substrate molecules n. The function L(n/M) describes this functionality. The function L(n/M) has some regions, where it shows linear dependence, but with increasing administration dosages it deviates more and more from a linear dependence.

In an embodiment, g(P) is P—or if the product is $CO_2$, g($P_{CO2}$) is $P_{CO2}$, respectively—and/or V(n/M) is 1 and/or h(n) is 1.

In the most simplest case, representing a further embodiment, when g($P_{CO2}$)=$P_{CO2}$, V(n/M)=1 and h(n)=1 the liver metabolic power is calculated by:

$$MetPow=cal*[F(^{13}CO_2,^{12}CO_2,t)-f(^{13}CO_2,^{12}CO_2,t)_{nat}]*P_{CO2}*(n/M^2)*L(n/M)$$

In an embodiment, it is possible to calculate F($^{13}CO_2$, $^{12}CO_2$,t) in the same manner like f($^{13}CO_2$,$^{12}CO_2$)$_{nat}$, e.g. by one of the two according equations indicated above The liver metabolic power MetPow can be used to determine the maximal possible liver capacity by variation of the dosage (n/M) and interpolation of the function L(n/M). In any case, the metabolic power can be seen as equivalent to the metabolic capacity of a selected enzyme. While liver metabolic power is here chosen as illustrative example, all of the above explanations can also be transferred to the metabolic power of an organ in general and also apply to the determination of the metabolic capacity of an enzyme without further deductions to the function or metabolic power of an organ.

In order to determine the product concentration various high-sensitive and time-resolved measurement methods such as for example infrared-absorption spectroscopy, mass spectrometry, nuclear magnetic resonance spectroscopy (NMR spectroscopy) or computer tomography (CT), for instance in the form of CT volumetry, can be used individually or in any combination with each other. By such a combination the respective effects of the individual measurement methods can be combined with each other to in this way be able to make supplemental or more accurate statements on the metabolic capacity of the enzyme.

Suitable substrates, which on the one hand can be metabolized by enzymes of the examined individual and the metabolites of which can be easily detected, are $^{13}C$-labeled methacetin, $^{13}C$-labeled phenacetin, $^{13}C$-labeled aminopyrine, $^{13}C$-labeled caffeine, $^{13}C$-labeled erythromycin and/or $^{13}C$-labeled ethoxycoumarin. The use of these substrates, individually or in combination, in a method according to the explanations above is also subject-matter of an aspect of this invention.

In an embodiment, dosages are about 0.1 mg to 10 mg per kilogram bodyweight of the individual, particularly 0.5 mg to 9 mg, particularly 1 mg to 8 mg, particularly 2 mg to 7 mg, particularly 3 mg to 6 mg and especially 4 mg to 5 mg per kilogram bodyweight of the individual.

In an embodiment of the present method the absolute content of a $^{13}C$-labeled metabolism product, particularly the $^{13}CO_2$ content, in the exhaled air is determined. Here, measuring the content of the $^{13}C$-labeled product, particularly of the $^{13}CO_2$ content, in the exhaled air can take place both in real time and continuously. A continuous determination of the concentration of the $^{13}C$-labeled metabolism product, particularly of the $^{13}CO_2$-concentration, in the exhaled air in the measuring instrument results in the detection of more data points, whereby a higher resolution and precision of the measurement curve, calculated from the detected data points, follows.

Many substrates, which would be suitable for the direct detection of a metabolism dynamics by determining the product concentration in the air exhaled by an individual, are unfortunately difficult to dissolve. That is not a disadvantage when these substrates are taken orally and are later activated in the blood by light induction (caged compounds). Alternative forms of administration in part are reliant on the fact that these substrates can be dissolved e.g. in an aqueous solution or a slightly volatile solution. For this purpose nanocarriers can be employed, which can be specifically modelled and consequently contain areas which can absorb the substrate in a sufficient form. The development of nanocarriers offers far-reaching possibilities and can be employed for breath analysis in infrared spectroscopy, mass spectrometry, CT and/or NMR spectroscopy.

If one does not want to rely on either caged compounds or nanocarriers, the use of a solubilizer such as for instance propylene glycol is recommendable to achieve a better solubility of the substrate. The use of an aqueous solution of $^{13}C$-methacetin and a solubilizer, particularly propylene glycol, in a method according to the explanations above is hence also subject-matter of an aspect of the present invention.

In an embodiment, the concentration of the solubilizer, particularly of the propylene glycol, is 10 to 100 mg/ml, particularly 20 to 80 mg/ml, particularly 30 to 70 mg/ml and especially 40 to 60 mg/ml, and the concentration of the $^{13}C$-methacetin is, in an embodiment, 0.2 to 0.6% weight by weight, particularly 0.3 to 0.5% weight by weight or about 0.4% weight by weight.

In an alternative embodiment the $^{13}C$-methacetin is employed in even higher concentration, namely in a concentration of more than 3% weight by weight, particularly more than 4% weight by weight, particularly more than 5% weight by weight. The concentration of the solubilizer here can lie in the ranges previously mentioned.

BRIEF DESCRIPTION OF THE DRAWINGS

Further details of aspects of the invention presently claimed will be further explained with the help of figures of exemplary embodiments.

DETAILED DESCRIPTION

Figure 1:
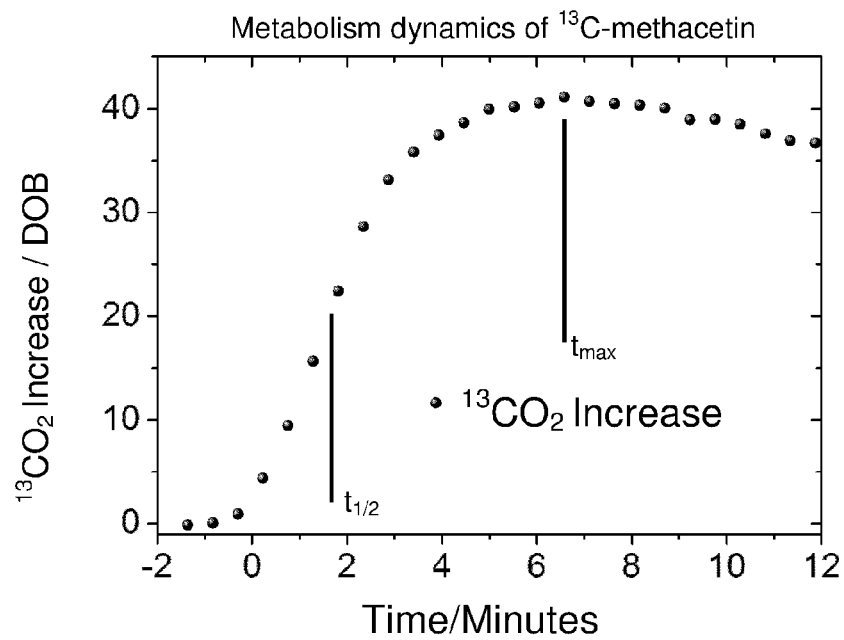
FIG. 1 shows a graphic representation of the kinetics of the concentration of a metabolized product over the measurement period and FIG. 2 shows a graphic representation of the non-linearity of the metabolic power of the liver determined according to an embodiment.

FIG. 1 shows a graphic representation of the measured product concentration in the air exhaled by an individual as a function of time. As substrate, $^{13}C$-labeled methacetin at a dose of 2 mg per kilogram bodyweight of the individual was administered to the individual, wherein the release period was shorter than 60 seconds. In the body of the individual the $^{13}C$-labeled methacetin was metabolized in the liver to paracetamol and $^{13}C$-labeled $CO_2$. The latter was detected as product in the air exhaled by the individual.

The diagram of FIG. 1 shows a rise in the $^{13}CO_2$-concentration in the form of the delta-over-baseline-value (DOB-value) in the exhaled air. 1 DOB here refers to a change of the $^{13}CO_2$-to-$^{12}CO_2$-ratio by a thousandth above the natural ratio. The obtained measured values, illustrated in FIG. 1, are subsequently fitted with a suitable model function. This is not yet illustrated in FIG. 1. From this model function—with a function equation familiar as such—different parameters can now be derived which specify the function. From these parameters conclusions can be drawn about the metabolic capacity of the examined enzyme system.

The time point of maximum methacetine metabolism ($t_{max}$, approximately at 6.5 minutes) and the time point of half-maximum methacetine metabolism ($t_{1/2}$, approximately at 1.5 minutes) are indicated in FIG. 1.

As methacetin is almost solely metabolized in the liver, with the specified metabolism dynamics it is possible to directly and immediately trace the metabolism of the administered substrate by the enzymes existing in the liver. In this way, the administered methacetin is demethylated by the enzyme CYP450 1A2 in the liver. By interpreting the rise kinetics of the administered methacetin and the parameters derived thereof it is now possible to directly determine the liver function. Here, for instance the value of the maximum product concentration in the exhaled air $P_{max}$ allows a statement to be made about the number of the healthy liver cells and the liver volume which is thus available for metabolism; whereas the rise in the form of the time constant(s) of the model function, fitted to the measured values, allows statements to be made about the entrance velocity of the substrate into the liver cells. The time constant(s) of the model function thus allows statements to be made about whether the liver is at all capable to absorb substrates. From the scattering of the time constants conclusions can be drawn about intercellular differences regarding a substrate susceptibility of the liver cells.

Figure 2:
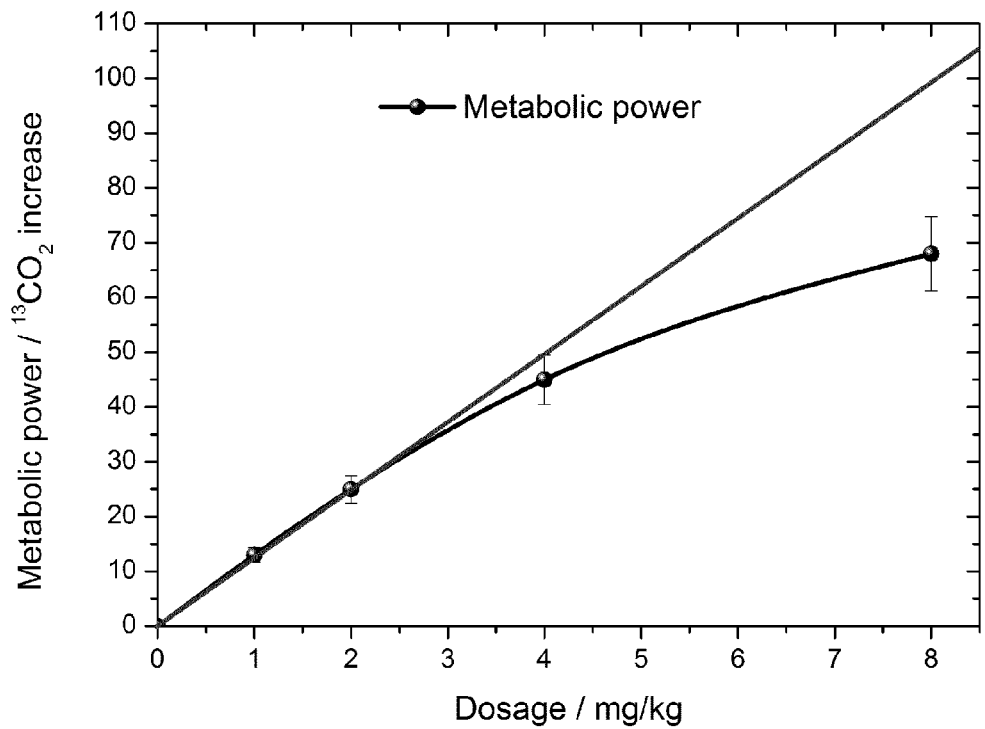

FIG. 2 shows the non-linearity of the metabolic power of the liver determined by methacetin metabolism. The metabolic power was determined according to the formulae indicated above for different methacetin metabolisms observed after methacetin administration in different dosages. Specifically, 1 mg $^{13}$C-labeled methacetin per kg bodyweight, 2 mg/kg, 4 mg/kg and 8 mg/kg were administered.

1 mg $^{13}$C-labeled methacetin per kg body weight M as well as 2 mg/kg show a linear dependence in the measured signals. Increase of administration to 4 mg/kg shows 10% deviation from the linear behaviour and administration of 8 mg/kg shows more than 20% deviation from the linear behaviour.

This non-linearity is expressed by the function L(n/M), wherein n denotes the number of substrate molecules, i.e. methacetin molecules, and M denotes the bodyweight in kg. This function L(n/M) forms part of the fitting curve represented in FIG. 2 by the interpolation curve between the single measurement points. The straight curve indicates a hypothetical interpolation curve if a linear dependence of the metabolic power on the dosage of the substrate was assumed and no non-linear effects were regarded.

The invention claimed is:

1. A method for determining the metabolic capacity of at least one enzyme, comprising the following steps:
predetermining a dosage of a substrate to be administered to an individual having the at least one enzyme such that the predetermined dosage provides for determining the metabolic capacity of the at least one enzyme, the predetermined dosage being sufficient for targeted induction of metabolism of the substrate;
administering the predetermined dosage of the substrate to the individual, wherein the substrate is available for metabolism within 60 seconds of the administering;
collecting air exhaled by the individual that has a product of the metabolized substrate;
measuring with a measuring apparatus a property of the product indicative of the concentration of the product in the exhaled air in order to determine the concentration of the product in the exhaled air;
using the determined concentration of the product, performing the following:
time-resolved determining of the concentration of the product in the air exhaled by the individual, wherein the product has been created by the metabolism of the substrate, previously administered to the individual, by the at least one enzyme of the individual and wherein the product concentration of the product of the metabolized substrate is determined essentially only at the least until the maximum product concentration in the air exhaled by the individual is reached,
fitting of a model function to measured values of the product concentration, which were obtained by the time-resolved determination of the product concentration between a start time and an end time,
determining the metabolic capacity of the at least one enzyme on the basis of parameters of the model function, which specify the model function,
wherein determining the metabolic capacity of the enzyme takes place on the basis of at least two parameters of the model function, with the proviso that the maximum value of the model function and the time constant of the model function are not selected as parameters at the same time, insofar as the model function is a mono-exponential function, and with the further proviso that the start time and/or the end time are not selected as parameters;
determining the state of health of the individual concerning specific bodily functions based on the metabolic capacity of the at least one enzyme; and
reporting the state of health of the individual.

2. The method according to claim 1, wherein the parameters are selected from the group comprising the maximum value of the model function, the i-th moment of the model function with i=1, 2, 3, 4, . . . , the j-th central moment of the model function with j=1, 2, 3, 4, . . . , the standard deviation of the model function, a time constant of the model function, the centre of gravity of the time constants, the mean deviation of the time constants from the centre of gravity, the variation of the time constants, the distribution of the time constants, the weighting of the time constants, the weighting of the distribution of the time constants, the weighting of the variation of the time constants.

3. The method according to claim 1, wherein the model function is a solution function of a first order differential equation, a solution function of a second order differential equation, a solution function of a third order differential equation, a solution function of a combination of differential equations of various orders or a multi-exponential function as a function of time.

4. The method according to claim 1, comprising flowing the exhaled air through the measuring apparatus, wherein the determination of the concentration of the product takes place with the exhaled air flowing through the measuring apparatus.

5. The method according to claim 4, wherein a flow rate of the exhaled air, flowing through the measuring apparatus which is used for determining the concentration, is determined.

6. The method according to claim 1, wherein to determine the concentration of the product the measuring apparatus has a breathing resistance below 100 mbar.

7. The method according to claim 1, wherein the entire exhaled air of at least one breath of the individual is used as exhaled air.

8. The method according to claim 1, wherein determining the concentration of the product takes place, while the individual is essentially in a resting position selected from a lying position or a sitting position.

9. The method according to claim 1, wherein determining the concentration of the product takes place, while the individual is in a lying or sitting position, in which the position of at least one of the legs and the upper part of the body of the individual is changed by less than 45 degrees, particularly by less than 30 degrees and especially by less than 15 degrees compared with the predetermined position.

10. The method according to claim 1, wherein determining the concentration of the product takes place by at least one of infrared-absorption spectroscopy, mass spectrometry, computer tomography and nuclear magnetic resonance spectroscopy.

11. The method according to claim 1, wherein the model function can be expressed by the following formula:

$$\text{MetPow} = \text{cal} * [F(\text{product},t) - f(\text{product},t)_{nat}] * g(P) * h(n) * L(n/M) * (n/M^2) * V(n/M),$$

wherein

MetPow denotes the metabolic capacity, cal is a constant taking into account corrections, F(product,t) is a function expressing the dynamics of exhaled product, $f(\text{product},t)_{nat}$ is a function expressing the natural abundance of the product in the air exhaled by the individual prior to substrate administration, g(P) is a function expressing the dependence of the product production rate P of the individual on the activity status of the individual, h(n) is a function expressing the number of product molecules generated per substrate molecule, L(n/M) is a function expressing a non-linear behaviour of the metabolic capacity dependent on the number of administered substrate molecules n, wherein M denotes the bodyweight of the individual, and V(n/M) is a function expressing dependencies due to different administration procedures of the substrate.

12. The method according to claim 11, wherein g(P)=P and/or h(n)=1 and/or V(n/M)=1.

13. The Method according to claim 1, wherein the model function can be expressed by the following formula:

$$\text{MetPow} = \text{cal} * [F(^{13}CO_2, ^{12}CO_2, t) - f(^{13}CO_2, ^{12}CO_2, t)_{nat}] * g(P_{CO2}) * h(n) * L(n/M) * (n/M^2) * V(n/M)$$

wherein

MetPow denotes the metabolic capacity, cal is a constant taking into account corrections, $F(^{13}CO_2, ^{12}CO_2, t)$ is a function expressing the dynamics of exhaled $^{13}CO_2$ as product or expressing the dynamics of exhaled ratio of $^{13}CO_2/^{12}CO_2$, $f(^{13}CO_2, ^{12}CO_2, t)_{nat}$ is a function expressing the natural abundance of $^{13}CO_2$ and $^{12}CO_2$ in the air exhaled by the individual prior to substrate administration, $g(P_{CO2})$ is a function expressing the dependence of the $CO_2$ production rate $P_{CO2}$ of the individual on the activity status of the individual, h(n) is a function expressing the number of $CO_2$ molecules generated per substrate molecule, L(n/M) is a function expressing a non-linear behaviour of the metabolic capacity dependent on the number of administered substrate molecules n, wherein M denotes the bodyweight of the individual, and V(n/M) is a function expressing dependencies due to different administration procedures of the substrate.

14. The method according to claim 13, wherein $g(P_{CO2})=P_{CO2}$ and/or h(n)=1 and/or V(n/M)=1.

15. The method according to claim 1, wherein at least one of methacetin, phenacetin, aminopyrine, caffeine, erythromycin and ethoxycoumarin, in each case $^{13}C$-labeled, is used as the substrate.

16. The method according to claim 1, wherein an aqueous solution of $^{13}C$-methacetin and a solubilizer is used as the substrate.

17. The method according to claim 16, wherein the concentration of the solubilizer is 10 to 100 mg/ml and the concentration of the $^{13}C$-methacetin is 0.2 to 0.6% weight by weight.

18. The method according to claim 16, wherein the concentration of the $^{13}C$-methacetin is more than 3% weight by weight.

19. A method for determining the metabolic capacity of at least one enzyme to determine a state of health of an individual, comprising the following steps:

time-resolved determining of the concentration of a product in the air exhaled by an individual, wherein the product has been created by a metabolism of a substrate, previously administered to the individual, by the at least one enzyme of the individual and wherein the product concentration is determined essentially only until the maximum product concentration in the air exhaled by the individual is reached, fitting of a model function to measured values of the product concentration, which were obtained by the time-resolved determination of the product concentration between a start time and an end time, determining the metabolic capacity of the enzyme on the basis of parameters of the model function, which specify the model function, wherein determining the metabolic capacity of the enzyme takes place on the basis of at least two parameters of the model function, with the proviso that the maximum value of the model function and the time constant of the model function are not selected as parameters at the same time, insofar as the model function is a mono-exponential function, and with the further proviso that the start time and/or the end time are not selected as parameters;

determining the state of health of the individual concerning specific bodily functions based on the metabolic capacity of the at least one enzyme and reporting the state of health of the individual.

20. The method of claim 19, further comprising determining a subsequent examination of the individual based on previously determined state of the health of the individual concerning specific bodily functions based on the metabolic capacity of the at least one enzyme.

21. The method of claim 1, further comprising determining a subsequent examination of the individual based on previously determined state of the health of the individual concerning specific bodily functions based on the metabolic capacity of the at least one enzyme.

22. The method of claim 1, further comprising providing the previously determined state of health of the individual to the individual.

23. The method of claim 21, further comprising providing the previously determined subsequent examination to the individual.

* * * * *